(12) United States Patent
Singh et al.

(10) Patent No.: US 6,455,702 B1
(45) Date of Patent: Sep. 24, 2002

(54) PROCESS FOR THE PRODUCTION OF N,N-CARBONYL DIIMIDAZOLE

(75) Inventors: Inder Pal Singh; Shradha Singh, both of Edmonton (CA)

(73) Assignee: Aims Fine Chemicals, Inc., Edmonton (CA)

( * ) Notice: Subject to any disclaimer, the term of this patent is extended or adjusted under 35 U.S.C. 154(b) by 0 days.

(21) Appl. No.: 09/983,338

(22) Filed: Oct. 24, 2001

Related U.S. Application Data

(63) Continuation of application No. 09/855,543, filed on May 16, 2001, now abandoned.

(51) Int. Cl.[7] .......................................... C07D 233/54
(52) U.S. Cl. ................................................ 548/314.4
(58) Field of Search ..................................... 548/314.4

(56) References Cited

U.S. PATENT DOCUMENTS

| 3,868,458 A | * | 2/1975 | Baker et al. ............... 424/273 |
| 3,991,071 A | * | 11/1976 | Brookes et al. ............. 260/309 |

FOREIGN PATENT DOCUMENTS

| WO | WO98/31672 | * | 7/1998 |
| WO | WO00/06551 | * | 10/2000 |

* cited by examiner

Primary Examiner—Floyd D. Higel
Assistant Examiner—Kamal Saeed
(74) Attorney, Agent, or Firm—Millen, White, Zelano & Branigan, P.C.

(57) ABSTRACT

A high purity N,N-Carbonyl diimidazole (I) is obtained by the reaction of Imidazole, general formula-II, and bis (trichloromethyl) carbonate. Synthesis of N,N-Carbonyl diimidazole (I) is described:

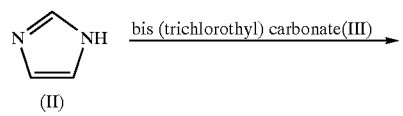

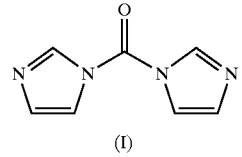

[i]H.A. Stabb, Angew.Chem., Int. Ed., Engl., 1,351 (1962); Angew.Chem., 7 1, 164, (1959)
[ii]H.A. Stabb, Angew.Chem., 71, 194, (1959).
[iii]U.S. Patent, US5380875
[iv]H.A. Stabb and W. Benz, Angew. Chem., 73, 66, (1961).
[v]H.A. Stabb, M. Luking and F.H. Durr, Chem. Ber., 95, 1275 (1962).
[vi]Spicer JA, Gamage SA, Atwell GJ, Finlay GJ, Baguley BC, Denny WA, Antica ncer Drug Des 1999 Jun; 14(3):281.
[vii]Ogata M, Matsumoto H, Shimizu S, Kida S, Shiro M, Tawara K, J Med Chem 1 987 Aug;30(8):1348
[viii]Matsuda T, Kondo A, Makino K, Akutsu T, ASAIO Trans 1989 Jul-Sep; 35(3) : 677-9
[ix]H.A. Stabb and K. Wendel, Chem. Ber.93, 2902 (1960)

20 Claims, No Drawings

PROCESS FOR THE PRODUCTION OF N,N-CARBONYL DIIMIDAZOLE

FIELD OF THE INVENTION

This application is a continuation of Appl. No. 09/855,543, filed on May 16, 2001 now abandoned.

The invention relates to a -process for the production of N,N-carbonyl diimidazole.

BACKGROUND OF THE INVENTION

The present invention is concerned with the production of N,N-Carbonyl diimidazole by a simple, safe and economically viable method utilizing commercially available and less toxic chemicals. The N,N-Carbonyl diimidazole is required in synthesis of activated esters of carboxylic acids to manufacture their amide[i] and ester[ii] derivatives by the reaction of active ester with an amine or a hydroxy function-bearing compound. Active esters are the intermediates in the synthesis of various pharmaceuticals such as Viagra™ (Sildenafil)[iii] etc., and other important chemicals, intermediates and products such as biologically active peptides or biopharmaceuticals. It is also used in the conversion of amines into corresponding isocyanate[iv] and acids into hydrazides[v]. Recently N,N-Carbonyl diimidazole has also been found useful in synthesis of anticancer[vi] and antifungal[vii] compounds and in the development of a novel artificial matrix with cell adhesion peptides for cell culture and artificial and hybrid organs[viii].

DESCRIPTION OF RELATED ART

A current method for the preparation of N,N-Carbonyl diimidazole is by the reaction of Imidazole dissolved in anhydrous tetrahydrofuran and dangerously lethal gas PHOSGENE to obtain crude Carbonyl-diimidazole in 88% yield[ix] as summarized below:

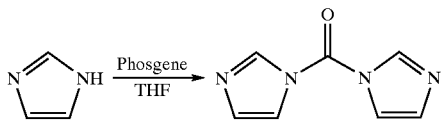

One of the serious drawbacks of this method is the gaseous and lethal nature of Phosgene, which is required in several folds excess to affect the completion of reaction. It is dangerous and uneconomical to store and handle phosgene.

It is the objective of the present invention to provide a safe and economic process for producing N,N-carbonyl diimidazole.

SUMMARY OF THE INVENTION

In accordance with the present invention, N,N-carbonyl diimidazole is produced by the reaction of imidazole with bis (trichloromethyl) carbonate with the exclusion of moisture. The reaction is summarized as follows:

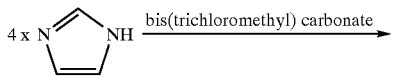

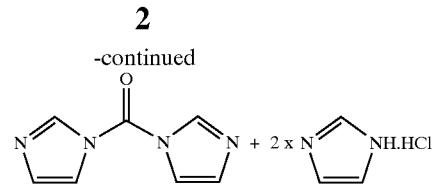

1. This invention provides an economical and safer method for the production of N,N-carbonyl diimidazole.
2. This invention provides methods for reacting imidazole with bis (trichloromethyl) carbonate in the presence or absence of a solvent.
3. It provides methods for the removal of byproduct imidazole hydrochloride and isolation of N,N-Carbonyl diimidazole.

DESCRIPTION OF THE PREFERRED EMBODIMENT

Reaction of imidazole with bis (trichloromethyl) carbonate produces carbonyl diimidazole and crystalline imidazole hydrochloride. Insoluble imidazole hydrochloride is removed from the reaction mixture quantitatively by filtration and the carbonyl diimidazole is recovered by removing the solvent or crystallization under cooling or a combination thereof.

The solvents used in the procedure of this patent can be an aromatic solvent i.e., benzene, toluene, xylene or their derivatives, a chlorinated solvent i.e., chloroform, dichloromethane, carbon tetrachloride or tetrahydrofuran (THF), dimethyl tetrahydrofuran or their derivatives or other solvents such as dimethylsulfoxide (DMSO), acetonitrile, dioxane or diphenyl ether or any aprotic solvent or a combination thereof.

The ratio of imidazole to bis (trichloromethyl) carbonate may vary from 0.05 to 2.0 moles of bis (trichloromethyl) carbonate for every mole of imidazole, however 0.83 moles of bis (trichloromethyl) carbonate for every mole of imidazole is preferred. The reaction temp. may vary from −10 to 70° C. but the preferred temp is between 20 and 40° C. The time for the reaction varies with solvents and the temperature used and, however a reaction time of 0.5–60 minutes is preferred.

The method of reacting imidazole with bis (trichloromethyl) carbonate can be varied. For example:

a) Imidazole and bis (trichloromethyl) carbonate are added simultaneously into an appropriate solvent and allowed to react and after the reaction is over byproduct imidazole hydrochloride is removed by filtration and N,N-Carbonyl diimidazole is recovered from the solvent following procedure described below.

b) A solution of imidazole is added to a solution of bis (trichloromethyl) carbonate or vice versa and allowed to react and after the reaction is over byproduct imidazole hydrochloride is removed by filtration and N,N-Carbonyl diimidazole is recovered from the solvent following procedure described below.

c) Imidazole and bis (trichloromethyl) carbonate in their solid forms are mixed mechanically in the absence of a solvent and allowed to react and after the reaction is completed, an anhydrous aprotic solvent as defined above is added to the molten reaction mixture. The separated solid imidazole hydrochloride is removed filtration and N,N-Carbonyl diimidazole is recovered from the solvent following procedure described below.

d) continuous and simultaneous addition and reaction of a solution of bis (trichloromethyl) carbonate and a solution of imidazole, comprising. removing by-product imidazole hydrochloride from the reaction stream continuously and recovering N,N-carbonyl diimidazole from the reaction stream;

Recovery of the N,N-Carbonyl Diimidazole from the Filtrate

The N,N-Carbonyl diimidazole can be isolated from the filtrate obtained from the processes described above in the following ways:

a) The solvent is removed by distillation under reduced pressure and temperatures lower then 55° C. and the crystallized N,N-Carbonyl diimidazole is collected by filtration and further drying under high vacuum and temperatures below 55° C. The overall yield of N,N-Carbonyl diimidazole is 75 to 99%.

b) Alternatively N,N-Carbonyl diimidazole can be removed from the reaction mixture by chilling the filtrate obtained above, the crystallized product was obtained by filtration and further drying of the solid under high vacuum and temperatures below 55° C. The overall yield of N,N-Carbonyl diimidazole obtained following above method is 75 to 99%.

c) N,N-Carbonyl diimidazole can also be recovered from the filtrate obtained above by a combination of evaporation of solvent and chilling to crystallize the product.

d) Total evaporation of the solvent under carefully controlled condition also provides N,N-Carbonyl diimidazole in quantitative yield.

e) N,N-Carbonyl diimidazole can also be isolated from the filtrate obtained at the end of reaction by diluting it with a solvent such as hexane or any other aprotic solvent, presence of which causes the precipitation of N,N-Carbonyl diimidazole from he reaction mixture followed by filtration and drying following the conditions described above.

This newly developed method is safer, efficient and environmentally friendly method due to the following facts:

Since bis(trichloromethyl) carbonate is a solid and is stable at, normal temperatures, it is safe to use under standard laboratory or manufacturing conditions. It can be weighed exactly and does not require to be used in more than required quantities, unlike phosgene, which due to its gaseous nature must be used in large excess. Bis (trichloromethyl) carbonate does not require any additional safety measures as required for phosgene and the training of the involved personnel. It easily decomposes in presence of water into harmless carbon dioxide and water-soluble hydrochloric acid. The hydrochloric acid solution can easily be converted into harmless brine solution.

The invention is exemplified by the following:

EXPERIMENTAL

General Conditions

All equipment used were dried in a oven at or above 100° C. All solvents were dried using standard practice. Reactions were performed utilizing standard three necked glass round bottom flask, equipped with a reflux condenser, inert gas inlet and outlet and a temperature probe. Inert and anhydrous atmosphere was maintained during the reaction by maintaining a slow and steady flow of pre-purified Nitrogen or Argon. The flow was monitored with the help of a bubbler mounted on the top of reflux condenser. Continuous reaction was carried out in a similar setup except the reaction flask was equipped with an additional outlet on the bottom half of the flask to allow the continuous removal of the reacted material. This outlet was attached to a glass filter funnel equipped with ground joints and medium sized cintered-glass fritt for the removal of imidazole hydrochloride from the reaction stream. The filtration funnel was attached to a receiving flask through a ground-glass joint. The flask was also attached to an inert-gas inlet and an outlet through a dryrite tube to maintain inert atmosphere and equilibrate the pressure. Reactants were stirred magnetically or mechanically. Reactants were added using addition funnels or metering addition pumps. Flask used for continuous reaction is hereinafter called "Continuous Flow Through Reactor or CFTR reactor)"

Example 1

A solution of 2.46 g bis-trichloromethyl carbonate (0.008 mole) in 50 ml of dry tetrahydrofuran was added drop wise at room temperature into a solution 6.89 g of imidazole (0.1 mole) dissolved in 50 ml of dry-tetrahydrofuran under a blanket of argon. The temperature was maintained under 40° C. by controlling the rate of addition. The separated crystalline imidazole hydrochloride was removed by filtration and the filtrate was evaporated under a stream of nitrogen to obtain N,N-carbonyl diimidazole as a white powder, yield: 3.96 g. NMR, ($CDCl_3$) δ: 8.212(s, 2H), 7.547(s, 2H), 7.251(s, 2H) ppm.

Example 2

A solution of 6.8 g of imidazole (0.1 mole) dissolved in 50 ml of dry tetrahydrofuran was added drop wise at room temperature into a solution 2.46 g of bis-trichloromethyl carbonate (0.008 mole) in 50 ml of tetrahydrofuran under a blanket of argon. The temperature was maintained at 40° C. by controlling the rate of addition. The separated crystalline imidazole hydrochloride was removed by filtration. The reaction volume was reduced under reduced pressure to 20 ml. N,N-carbonyl diimidazole was crystallized from the solution by cooling and was collected by filtration. The solid product was then dried under high vacuum to obtain flaky white crystalline N,N-carbonyl diimidazole, yield: 3.84 g. NMR, ($CDCl_3$) δ: 8.212(s, 2H), 7.547(s, 2H), 7.251(s, 2H) ppm.

Example 3

A solution of 2.46 g bis-trichloromethyl carbonate (0.008 mole) in 60 ml of dry dichloromethane was added drop wise at room temperature into a solution 6.8 g of imidazole (0.1 mole) dissolved in 60 ml of dry-dichloromethane under a blanket of argon. The temperature was maintained under the boiling point of dichloromethane by controlling the rate of-addition. The separated crystalline imidazole hydrochloride was removed by filtration. The reaction volume was reduced to 20 ml. N,N-carbonyl diimidazole was crystallized from the solution on cooling and was collected by filtration. The solid product was then dried under vacuum to obtain flaky white crystalline N,N-carbonyl diimidazole, yield: 3.89 g. NMR, ($CDCl_3$) δ: 8.212(s, 2H), 7.547(s, 2H), 7.251(s, 2H) ppm.

Example 4

A solution of 6.8 g of imidazole (0.1 mole) dissolved in 60 ml of dry dichloromethane was added drop wise at room temperature into a solution 2.46 g bis-trichloromethyl carbonate (0.008 mole) in 60 ml of dry-dichloromethane under a blanket of argon. The temperature was maintained under the boiling point of dichloromethane by controlling the rate of addition. The separated crystalline imidazole hydrochloride was removed by filtration and the solvent was removed under stream of nitrogen and temperatures below 50° C. to obtain N,N-carbonyl diimidazole as a white powder, yield; 3.90 g. NMR, (CDCl$_3$) δ: 8.212(s, 2H), 7.547(s, 2H), 7.251(s, 2H) ppm.

Example 5

A solution of 2.46 g bis-trichloromethyl carbonate (0.008 mole) in 20 ml of dry dichloromethane was added drop wise at room temperature into a solution 6.8 g of imidazole (0.1 mole) dissolved in 60 ml of dry-dichloromethane under a blanket of argon. The temperature was maintained under the boiling point of dichloromethane by controlling the rate of addition. The separated crystalline imidazole hydrochloride was removed by filtration. The reaction volume was reduced to 20 ml by evaporation under vacuum. N,N-carbonyl diimidazole was crystallized from the solution on cooling and was collected by filtration. The solid product was then dried under vacuum to obtain flaky white crystalline N,N-carbonyl diimidazole, yield:3.85 g. NMR, (CDCl$_3$) δ: 8.212 (s, 2H), 7.547(s, 2H), 7.251(s, 2H) ppm.

Example 6

A solution of 6.8 g of imidazole (0.1 mole) dissolved in 60 ml of dry dichloromethane was added drop wise at room temperature into a solution 2.46 g bis-trichloromethyl carbonate (0.008 mole) in 20 ml of dry dichloromethane under a blanket of argon. The temperature was maintained under 35° C. by controlling the rate of addition. The separated. crystalline imidazole hydrochloride was removed by filtration and the filtrate was evaporated under normal pressure and blanket of nitrogen to obtain flaky white crystals of N,N-carbonyl diimidazole, yield: 3.91 g. NMR, (CDCl$_3$) δ: 8.212(s, 2H), 7.547(s, 2H), 7.251(s, 2H) ppm.

Example 7

A solution of 2.46 g bis-trichloromethyl carbonate (0.008 mole) in 100 ml of dry chloroform was added drop wise at room temperature into a solution 6.8 g of imidazole (0.1 mole) dissolved in 100 ml of dry- chloroform under a blanket of argon. The temperature was maintained under 35° C. by controlling the rate of addition. The separated crystalline imidazole hydrochloride was removed by filtration and the filtrate was evaporated under normal pressure and blanket of nitrogen to obtain flaky white crystals of N,N-carbonyl diimidazole, yield 3.88 g. NMR, (CDCl$_3$) δ: 8.212 (s, 2H), 7.547(s, 2H), 7.251(s, 2H) ppm.

Example 8

A solution of 6.8 g of imidazole (0.1 mole) dissolved in 100 ml of dry chloroform was added drop wise at room temperature into a solution 2.46 g bis-trichloromethyl carbonate (0.008 mole) in 100 ml of dry-chloroform under a blanket of argon. The temperature was maintained under 35° C. by controlling the rate of addition. The separated crystalline imidazole hydrochloride was removed by filtration. The reaction volume was reduced to 15 ml. N,N-carbonyl diimidazole was crystallized from the solution on cooling and was collected by filtration. The solid product was then dried under high vacuum to obtain flaky white crystalline N,N-carbonyl diimidazole, yield 2.83 g. NMR, (CDCl$_3$) δ: 8.212(s, 2H), 7.547(s, 2H), 7.251(s, 2H) ppm.

Example 9

2.46 g of solid bis-trichloromethyl carbonate (0.008 mole) and 6.8 g of solid imidazole (0.1 mole) were mechanically mixed under blanket of argon in a round bottom flask. The temperature was maintained under 35° C. by external cooling. The molten material was allowed to cool and then diluted with dry dichloromethane. The separated crystalline imidazole hydrochloride was removed by filtration. The filtrate volume was reduced to 20 ml. N,N-carbonyl diimidazole was crystallized from the solution on cooling and was collected by filtration. The solid product was then dried under high vacuum to obtain flaky white crystalline N,N-carbonyl diimidazole, yield: 2.86 g. NMR, (CDCl$_3$) δ: 8.212(s, 2H), 7.547(s, 2H), 7.251(s, 2H) ppm.

Example 10

2.46 g of solid bis-trichloromethyl carbonate (0.008 mole) and 6.8 g of solid imidazole (0.1 mole) were mechanically mixed under blanket of argon in a round bottom flask. The temperature was maintained under 35° C. by external cooling. The molten material was allowed to cool and then diluted with tetrahydrofuran. The separated crystalline imidazole hydrochloride was removed by filtration and the filtrate was evaporated under vacuum to obtain N,N-carbonyl diimidazole, yield: 3.85 g. NMR, (CDCl$_3$) δ: 8.212(s, 2H), 7.547(s, 2H), 7.251 (s, 2H) ppm.

Example 11

2.46 g of solid bis-trichloromethyl carbonate (0.008 mole) and 6.8 g of solid imidazole (0.1 mole) were mechanically mixed under blanket of argon in a round bottom flask. The temperature was maintained under 35° C. by external cooling. The molten material was allowed to cool and then diluted with dichloromethane (50 ml). The separated crystalline imidazole hydrochloride was removed by filtration and the filtrate was evaporated under vacuum to obtain N,N-carbonyl diimidazole, yield: 3.91 g. NMR, (CDCl$_3$) δ: 8.212(s, 2H), 7.547(s, 2H), 7.251(s, 2H) ppm.

Example 12

A solution of 68 g (1.0 mole) of imidazole in dry dichloromethane (800 ml) and a solution of bis-trichloromethyl carbonate 296.75 g(1.0mole) in dry dichloromethane (800 ml) were introduced saparately and simultaneously at a rate of 10 ml per minute into a CFTR reactor. The effluent from the reactor was passed through the filtration chamber where by-product, imidazole hydrochloride, was removed continuously and the clear filtrate that was emerged from the filtration chamber was collected. The filtrate was evaporated to obtain N,N-carbonyl diimidazole. The yield was 39.6 g. NMR, (CDCl$_3$) δ: 8.212(s,2H), 7.547(s, 2H), 7.251(s, 2H) ppm.

Example 13

A solution of 68 g (1.0 mole) of imidazole in dry dichloromethane (800 ml) and a solution of bis-trichloromethyl carbonate 296.75 g(1.0 mole) in dry dichloromethane (800 ml) were added separately and simultaneously at a rate of 20 ml per minute into a CFTR reactor. The temperature of the reaction was maintained at 35° C. by external cooling. The effluent from the reactor was passed through the filtration chamber where by-product, imidazole hydrochloride, was removed continuously. The clear filtrate that emerged from the filtration chamber was evaporated continuously to obtain solid N,N-carbonyl diimidazole. Total yield was 39.10 g. NMR, (CDCl$_3$) δ: 8.212(s, 2H), 7.547(s, 1 2H), 7.251(s, 2H) ppm.

Experiment 14

A solution of 1360 g (2.0 mole) of imidazole in dry dichloromethane (16000 ml) and a solution of bis-trichloromethyl carbonate 5935 g(2.0 mole) in dry dichloromethane (8000 ml) were added separately and simultaneously at a rate of 20 ml per minute into a CFTR reactor. The temperature of the reaction was maintained at 35° C. by external cooling. The effluent from the reactor was passed through the filtration chamber where by-product, imidazole hydrochloride, was removed continuously. The clear filtrate that emerged from the filtration chamber was chilled to affect crystallization of N,N-carbonyl diimidazole, which was collected by filteration and dried under vacumme to produce white crystalline N,N-Carbonyl diimidazole. The total yield was 570 g. NMR, (CDCl$_3$) δ: 8.212(s, 2H), 7.547(s, 2H), 7.251(s, 2H) ppm.

The embodiments of the invention in which an exclusive property or privilege is claimed are defined as follows:

1. A method for producing N,N-carbonyl diimidazole comprising:

reacting imidazole with bis-trichloromethyl carbonate to produce N,N-carbonyl diimidazole.

2. The method as set forth in claim 1 wherein:

a solution of imidazole is added into a solution of bis-trichloromethyl carbonate.

3. The method as set forth in claim 1 wherein:

a solution of bis-trichloromethyl carbonate is added into a solution of imidazole.

4. The method as set forth in claim 1 wherein:

the imidazole and bis-trichloromethyl carbonate are each mixed in their solid forms to react.

5. The method as set forth in claim 1 wherein:

the imidazole an d bis-trichloromethyl carbonate are simultaneously added into appropriate solvent, dissolved and reacted.

6. The method as set forth in claim 1 wherein:

a solution of imidazole and a solution of bis-trichloromethyl carbonate are continuously and simultaneously added together and reacted.

7. The method as set forth in claim 1 wherein:

a solution of imidazole and a solution of bis-trichloromethyl carbonate are continuously and simultaneously added together and, reacted to form a reaction stream containing insoluble imidazole hydrochloride; and comprising
a) continuously removing the imidazole hydrochloride from the reaction stream; and
b) recovering purified N,N-carbonyl diimidazole.

8. The method as set forth in claim 1 wherein:

solid bis-trichloromethyl carbonate is added into a solution of imidazole.

9. The method as set forth in claim 1 wherein:

solid imidazole is added into a solution of bis-trichloromethyl carbonate.

10. The method as set forth in claim 1 comprising:

reacting imidazole and bis-trichloromethyl carbonate in the presence of at least one anhydrous aprotic solvent.

11. The method as set forth in claim 1 comprising filtering the reaction mixture to remove the imidazole hydrochloride and produce a filtrate.

12. The method as set forth in claim 7 comprising:

filtering the reaction stream to remove the imidazole hydrochloride and produce a filtrate.

13. The method as set forth in claim 11 comprising:

recovering purified N,N-carbonyl diimidazole from the filtrate by cooling, crystallization and filtration.

14. The method as set forth in claim 11 comprising:

removing solvent from the filtrate under vacuum and at a temperature below 35° C. to recover purified N,N-Carbonyl diimidazole.

15. The method as set forth in claim 12 comprising:

recovering purified N,N-carbonyl diimidazole from the filtrate by cooling, crystallization and filtration.

16. The method as set forth in claim 12 comprising:

removing solvent from the filtrate under vacuum and at a temperature below 35° C. to recover purified N,N-Carbonyl diimidazole.

17. A process according to claim 1, conducted under the substantial exclusion of moisture.

18. A process according to claim 5, wherein said appropriate solvent is an aromatic solvent i.e., benzene, toluene, xylene or their derivatives, a chlorinated solvent i.e., chloroform, dichloromethane, carbon tetrachloride or tetrahydrofuran (THF), dimethyl tetrahydrofuran or their derivatives or other solvents such as dimethylsulfoxide (DMSO), acetonitrile, dioxane or diphenyl ether or any aprotic solvent or a combination thereof.

19. A process according to claim 1, conducted continuously.

20. A process according to claim 17, wherein a slow steady flow of pre-purified nitrogen or argon is employed in order to maintain substantially anhydrous conditions.

* * * * *